(12) United States Patent
Fry

(10) Patent No.: US 6,755,821 B1
(45) Date of Patent: Jun. 29, 2004

(54) SYSTEM AND METHOD FOR STIMULATION AND/OR ENHANCEMENT OF MYOCARDIAL ANGIOGENESIS

(75) Inventor: Stephen M. Fry, Princeville, HI (US)

(73) Assignee: Cardiocavitational Systems, Inc., Princeville, HI (US)

( * ) Notice: Subject to any disclaimer, the term of this patent is extended or adjusted under 35 U.S.C. 154(b) by 0 days.

(21) Appl. No.: 09/457,490

(22) Filed: Dec. 8, 1999

Related U.S. Application Data

(60) Provisional application No. 60/111,347, filed on Dec. 8, 1998.

(51) Int. Cl.[7] .............................................. A61B 19/00
(52) U.S. Cl. ............................... 606/15; 606/7; 606/10; 606/13; 606/46; 604/20; 604/22
(58) Field of Search .............................. 604/19, 20, 22; 606/3, 7, 10–16, 167–170, 185, 41, 45, 46

(56) References Cited

U.S. PATENT DOCUMENTS

| | | | |
|---|---|---|---|
| 4,223,676 A | | 9/1980 | Wuchinich et al. |
| 4,445,892 A | * | 5/1984 | Hussein et al. .................. 606/7 |
| 4,960,108 A | * | 10/1990 | Reichel et al. .............. 606/127 |
| 5,031,626 A | | 7/1991 | Hassler et al. |
| 5,281,231 A | * | 1/1994 | Rosen et al. ................. 606/128 |
| 5,295,484 A | | 3/1994 | Marcus et al. |
| 5,368,591 A | | 11/1994 | Lennox et al. |
| 5,524,620 A | | 6/1996 | Rosenschien |
| 5,590,657 A | | 1/1997 | Cain et al. |
| 5,601,526 A | * | 2/1997 | Chapelon et al. .............. 601/2 |
| 5,827,203 A | | 10/1998 | Nita |
| 5,873,845 A | | 2/1999 | Cline et al. |
| 5,885,272 A | | 3/1999 | Aita et al. |
| 5,925,012 A | * | 7/1999 | Murphy-Chutorian et al. ... 604/20 |
| 5,944,687 A | | 8/1999 | Benett et al. |

FOREIGN PATENT DOCUMENTS

| | | |
|---|---|---|
| EP | 0 834 287 A1 | 4/1998 |
| WO | WO 90/09762 | 9/1990 |
| WO | WO 98/16157 A1 | 4/1998 |
| WO | WO 98/51224 A2 | 11/1998 |
| WO | WO 99/13784 A1 | 3/1999 |
| WO | WO 99/13786 A1 | 3/1999 |

OTHER PUBLICATIONS

Nadine Barrie Smith and Kettervo Hynynen, *The Feasibility of Using Focused Ultrasound for Transmyocardial Revascularization*, Ultrasound in Med. & Biol. vol. 24, No. 7, 1998, pp. 1045–1054.

* cited by examiner

Primary Examiner—David M. Shay
(74) Attorney, Agent, or Firm—Gordon & Rees LLP

(57) ABSTRACT

Shock-waves are applied using a combination lithotripsy probe/balloon system, comprising a needle and cannular balloon which can be inserted through the skin at a point between the ribs into the cavity beneath the chest wall and overlying the heart. Alternatively, the shock-wave can be administered extracorporally or via a catheter. A fluid injector is connected to the balloon, allowing it to be inflated with saline or other appropriate fluid to fill the space (for transmission of shock waves and/or to displace tissue—such as lung) and contact the surface of the heart. A shock-wave (acoustic) generator is used to generate shock-waves through the lithotripsy probe, through the fluid and into the myocardial tissue. The fluid provides a uniform medium for transmission of the acoustic energy, allowing precise focus and direction of the shock-wave to induce repeatable cavitation events, producing small fissures which are created by the cavitation bubbles. In this case, channels would not be 'drilled' into the heart muscle, minimizing trauma to the tissue while still creating conditions that will stimulate increased expression of angiogenic growth factors.

11 Claims, 2 Drawing Sheets

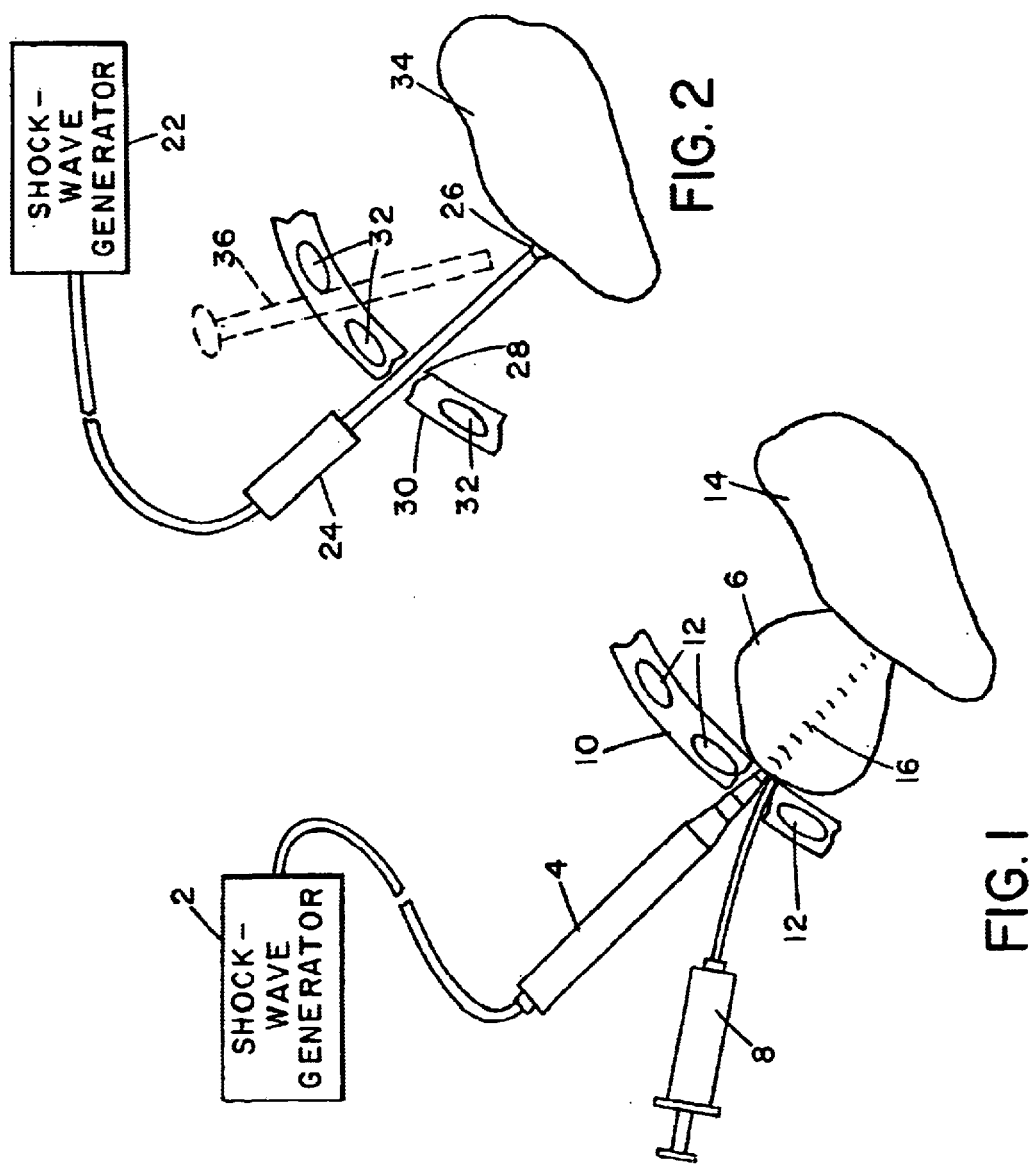

SYSTEM AND METHOD FOR STIMULATION AND/OR ENHANCEMENT OF MYOCARDIAL ANGIOGENESIS

RELATED APPLICATIONS

This application claims priority to U.S. Provisional Application Serial No. 60/111,347, filed Dec. 8, 1998, the disclosure of which is incorporated herein in its entirety.

BACKGROUND OF THE INVENTION

Coronary artery disease ("CAD") is a leading cause of death worldwide. More than 6 million Americans have CAD, of which some 1.5 million suffer heart attacks (myocardial infarction), resulting in 500,000 deaths and nearly 1 million hospitalizations annually in the U.S. CAD is characterized by narrowing of the arteries that feed the heart muscle ("myocardium"); without adequate blood supply, the tissue becomes starved for oxygen ("ischemic"), and the heart does not pump as efficiently. A heart attack (which usually indicates a complete blockage of a coronary artery) can result in a portion of the heart muscle being ischemic for a prolonged time and then dying, which can permanently reduce the patient's ability to perform exercise, such as walking. The treatment of CAD includes preventive measures (modification of diet and/or exercise, reduction in hypercholesterolemia through various drugs, etc.), minimally invasive clearing of arteries (angioplasty, atherectomy, intravascular stenting), and surgical bypass of the diseased artery(ies) (coronary artery bypass surgery, "CABG"). While preventive measures have helped to reduce the number of CAD patients, CAD remains one of the greatest health problems in the world today.

Angioplasty and related catheter-based procedures can unblock some arteries, but the blockages, or "stenoses", typically return, a condition known as "restenosis," within 6–18 months due to intimal hyperplasia, which is creation of scar tissue from the traumatic vessel wall damage during the angioplasty procedure. The use of stents (metal or polymer tubes or coils which hold the artery open) has decreased the restenosis rate by about one half. Radioactive devices (catheters and stents) are being developed to further reduce the restenosis rate. However, angioplasty has fundamental limitations, which are unlikely to ever be solved completely. These include inability to reach smaller vessels, morbidity associated with failed angioplasty procedures, poor success rate in certain vessels, e.g., saphenous vein grafts, and general inability to completely revascularize the heart muscle (myocardium). Approximately 800,000 coronary angioplasty procedures are performed annually in the U.S.

Coronary artery bypass procedures are performed on approximately 400,000 people in the U.S. annually, and nearly 800,000 people worldwide.

Although the primary result of CABG is generally satisfactory, the saphenous veins used in most patients become blocked 10–15 years after surgery. Also, CABG procedures are very traumatic, and carry a risk of mortality around 1–3%. Although "heart port", "off-pump", and other minimally invasive types of CABG procedures are being developed, they are all quite invasive and/or utilize a pump and oxygenator ("heart-lung machine"), which introduces additional trauma to the patient.

Transmyocardial revascularization (TMR) using a laser (sometimes referred to as TMLR, LTMR, PMR, PTMR, or DMR) has been developed over the past decade, initially by a company called PLC Systems, Inc., of Franklin, Mass. PLC's system utilizes a high power (800–1000 W) carbon dioxide ($CO_2$) laser which drills small channels in the outside (epicardial) surface of the myocardium in a surgical procedure. The holes communicate with the left ventricle, which delivers blood directly to the heart muscle, mimicking the reptilian heart. Many other companies are developing laser TMR systems, most introducing the laser light via optical fibers through a flexible catheter, making the procedure less-invasive. These companies include Eclipse Surgical Technologies, Inc., of Sunnyvale, Calif., and Helionetics, Inc., of Van Nuys, Calif. The Eclipse TMR system uses a Ho:YAG laser with a catheter-delivered fiber optic probe for contact delivery to the myocardium. The Helionetics system is based on an excimer laser. In addition to the holmium:YAG and excimer lasers, and other types of lasers have been proposed for TMR.

While the channels created during TMR are known to close within 2–4 weeks, most patients tend to improve clinically over a period of 2–6 months.

Such clinical improvement may be demonstrated by reduction in chest pain ("angina"), and a dramatic increase in exercise tolerance ("ETT", or treadmill test). The mechanism of laser TMR is not fully understood, but it is postulated that the laser causes near-term relief of angina through denervation or patent channels, with subsequent long-term clinical improvement due to angiogenesis, i.e., growth of new blood vessels, mainly capillaries, which perfuse the heart muscle. These new "collateral" vessels enable blood to reach downstream ("distal") ischemic tissues, despite blockages in the coronary arteries. Some of the possible mechanisms by which the laser induces angiogenesis could include activation of growth factors by light, thermal, mechanical, cavitational or shockwave means. In fact, all lasers which have been successfully used for TMR are pulsed systems, and are known to create shock waves in tissue, and resulting cavitation effects.

Cavitation can be induced in a liquid-rich environment like tissue. An opening or cavity can be created in a fluid by thermal vaporization or an rapid movement of a solid through the liquid (such as explosive expansion of a gas bubble formed in the tissue). When energy is focused into a small area of a liquid in a short time, e.g., <1 ms, the temperature can rapidly rise above boiling temperature and vapor is formed. Typically, the vapor volume is over 1000 times the original liquid volume. The vapor is formed at very high pressure and an explosive vapor bubble will be created, rapidly expanding to equalize the internal bubble pressure to ambient pressures. This bubble creates an opening in the liquid (or tissue) environment. While the bubble is expanding, the temperature inside will decrease and drop below the boiling point. The vapor then turn backs into liquid. Due to the momentum of expansion however, the bubble expands, further creating a semi-vacuum. At some point, the negative pressure overcomes the momentum of expansion, and the process becomes an implosion. Like the expansion, the implosion can be very fast, inducing a high momentum in the surrounding liquid. The motion of the liquid during implosion will be spherically symmetric, concentrated in the middle of the imploding bubble. The collision at the moment of total implosion is very forceful and is capable of creating supersonic density waves in the liquid, or "shock-waves." If the energy release at the start of bubble formation is also very concentrated, a shock-wave can also be generated at the very start of the bubble.

Cavitation bubbles can also be formed by focusing shock waves into the liquid/tissue from an external shock wave generator. Shock-wave generators create locally very high temperatures inducing plasmas in liquids. The heat transfer to the environment subsequently creates a vapor bubble inducing the process as described above.

Another method to induce cavitation effects in liquid is by displacing the liquid at high speed by moving a solid object through the liquid. Because a delay occurs before the liquid can fill in the gap behind the object moving through the liquid, a vacuum will briefly form. The liquid filling this vacuum will be accelerated to very high speeds. At the instant the gap is filled, the liquid collides within the center of the gap, forming a shock-wave. In tissue environment, cells are sucked from their matrix by the rapidly moving liquid causing the tissue itself to effectively become liquefied.

Catheters have been previously developed which can deliver high intensity ultrasound energy to the coronary arteries for the purpose of removing thrombus (blood clots) and/or atherosclerotic plaque (see, e.g., U.S. Pat. No. 5,524,620 of Rosenschein) [note that these catheters are quite different from the intravascular imaging devices that use low intensity ultrasonic signals to probe and image arterial cross-sections]. These catheters could be modified to deliver ultrasound energy to the myocardium.

Catheters have also been previously developed which can remove tissue via spark erosion, electrical discharge, or other shock wave producing technologies. These shock waves, if of sufficient amplitude in a localized region, can create a cavitation effect. This is the principle behind shock-wave lithotripters, which are used to non-invasively break-up kidney and ureteral stones ("calculi"). Such systems are known in the art (particularly in the fields of urology and gastroenterology), but can produce severe tissue damage—typically much greater than the damage produced by laser TMR.

Initially, TMR was performed on patients who were not acceptable candidates for angioplasty or bypass surgery. It is hoped that TMR could be a replacement for bypass surgery, for those patients who's arteries continue to restenose after angioplasty. Ultimately, with a non-invasive TMR approach as described herein, TMR could be used on CAD patients instead of (or prior to) angioplasty, CABG or any other revascularization procedure. In addition to the possibility of the TMR procedure replacing conventional revascularization procedures, it is currently being used as an adjunct to CABG surgery; in this case, areas of the myocardium where blood flow cannot be completely restored using surgical bypass (e.g., because the vessels are too small or too clogged) can be treated with TMR, enhancing the blood flow to these distal regions, and improving the overall outcome of the CABG procedure.

In parallel with laser TMR developments have been developments of angiogenic growth factors, which can also stimulate small capillary growth ("angiogenesis") in heart muscle. Vascular endothelial growth factor ("VEGF"), angiopoetin-1 and -2, basic fibroblast growth factor (bFGF), and other growth factors are now being studied, with therapeutic angiogenesis being demonstrated in animal models. A few studies have progressed to testing on humans. Although it is too early to make a definitive conclusion, it appears that angiogenesis created by these growth factors may help CAD patients clinically. However, the administration of these drugs, once they are approved by the FDA, will either be systemic—opening the potential for unwanted vessel growth, for example in the eye or in tumors; or they may require direct introduction of the growth factor(s) into the myocardium. Therefore, companies are developing devices for injecting growth factors into heart muscle, including lasers, catheter-based systems, and other devices.

Current technologies for revascularizing the heart—including all commercialized TMR approaches to-date—have severe limitations. Laser TMR systems are very expensive ($250,000–500,000). The original (PLC) system requires open chest surgery, which is nearly as traumatic as CABG surgery. Some catheter-based TMR systems have recently been approved by the FDA, but they are also expensive ($250,000 or more for the laser, and $1000 or more for the catheter). Catheter-based systems may also require a guidance technique, such as electrical mapping, which introduces further costs.

The development of growth factors, and the delivery of genes or proteins which introduce or activate specific growth factors is ongoing. Many growth factors are combined with a recombinant adenovirus to provide an efficient gene delivery vector for a variety of cell types and tissues. However, the long-term complications of the use of these adenoviral vectors, e.g., cancerous growths, and systemic effects, e.g., viral infection, are currently unknown. If direct targeting to the myocardium is required, catheter-based systems may be necessary. Some of these catheter systems even utilize an expensive laser to make channels or pockets, where the drug is injected.

While the mechanism of action of TMR is not fully understood, it must rely on one of several possible effects of pulsed lasers: light, heat, and/or shock waves (and resulting cavitation). Neither light nor heat has previously shown any ability to improve the condition of CAD patients, although various surgical instruments using heat have been used for decades in heart surgery. Therefore, the most likely characteristic of laser energy which could cause angiogenesis is the cavitation resulting from shock waves produced by explosive vaporization of tissue using high power pulsed laser systems.

As cavitation phenomena appear to be the likely source of trauma which stimulates expression of natural growth factors responsible for myocardial angiogenesis, a rational and cost-effective approach to TMR would be to select an appropriate shock wave generator, and a delivery system that can utilize these shock waves to create cavitation in the myocardium. The laser may not be the best candidate for this function. Lasers produce both shock waves and heat, and heat has often been found to be 'bad' for the heart (e.g., thermal angioplasty). Lasers also usually represent the most expensive technology that can provide a given physical result, and current TMR systems are not cost-effective (hospitals are currently paying $500,000 for a laser to generate shock waves that could also be obtained using a $50,000 electromechanical generator system).

Studies using focused ultrasound for TMR were first reported by Smith and Hynynen in 1998. (Ultrasound in Medicine & Biology, Vol. 24, No. 7, 1998, pp. 1045–1054.) Ultrasonic transducers were used to deliver focused ultrasound energy to animal myocardium. The authors speculate that, potentially, a phased array of transducers could be used to focus shock waves into human hearts (around or between the ribs) completely non-invasively. Mechanisms of achieving the desired results in the experimental animals included tissue destruction via thermal vaporization or cavitation. However, while a completely non-invasive procedure would be a significant advantage, this should not come at the cost of diminished effectiveness. Access to the heart by transmission of shock waves to produce cavitation is limited to a relatively small area of the myocardium. Shock waves cannot be focused effectively through tissues of different densities, such as bone, or through air spaces (e.g., lungs or thoracic cavity). Furthermore, since the energy must pass through inhomogeneous tissues (i.e., tissues of varying density, such as bone), the ultrasonic waves may be non-uniformly diffracted, refracted and/or reflected, resulting in possible variation in the focus or other distortion of the beam which may prevent the shock waves from causing cavitation. Shock waves also must be transmitted through a liquid or solid material, and are not effectively transmitted through air spaces, such as in the lungs or thoracic cavity. Therefore, it becomes extremely difficult to treat a sufficient area of myocardium to generate the desired angiogenic result to improve clinical outcome. In TMR procedures, where many traumatic sites must be created (typically, channels on the order of 1 mm are typically made), repeatability is an important issue. Thus, while the concept of using focused ultrasound for TMR has been shown feasible in an animal laboratory, a number of issues must be addressed before ultrasound or other shock wave (cavitational) approaches can be made to be safe and effective for TMR in actual human patients. Accordingly, the need remains for relatively inexpensive surgical, minimally invasive, and non-invasive systems for performing TMR.

SUMMARY OF THE INVENTION

It is the object of this invention to provide system and method for revascularizing the heart utilizing cavitation effects to trigger and enhance angiogenesis in the myocardium.

It is further an object of this invention to induce such cavitation effects using either surgical or minimally invasive methods, either by a percutaneous, endoscopic or catheter-based device.

In an exemplary embodiment, the transcutaneous application of shockwaves is achieved using a combination lithotripsy probe/balloon system, comprising a needle and cannular balloon which can be inserted through the skin at a point between the ribs into the cavity beneath the chest wall and overlying the heart. A fluid injector is connected to the balloon, allowing it to be inflated with saline or other appropriate fluid to fill the space (for transmission of shock waves and/or to displace tissue—such as lung) and contact the surface of the heart. A shock-wave (acoustic) generator is used to generate shock-waves through the lithotripsy probe, through the fluid and into the myocardial tissue. The fluid provides a uniform medium for transmission of the acoustic energy, allowing precise focus and direction of the shock-wave to induce repeatable cavitation events, producing small fissures which are created by the cavitation bubbles. In this case, channels would not be 'drilled' into the heart muscle, minimizing trauma to the tissue while still creating conditions that will stimulate increased expression of angiogenic growth factors. The fluid in the balloon also stabilizes the myocardium, reducing variations which can occur do to movement of the heart as it beats, since the balloon remains in contact with the surface of the heart throughout the procedure. Visualization of the target area can be achieved using known methods including an integrated shock wave generating/transmitting endoscope or a separate optical or video-based viewing endoscope.

In another exemplary embodiment, a transcutaneous endoscopic probe has a transducer disposed at its distal end which is inserted through a small incision between the ribs, such as in CABG procedures ("midcab"), so that the distal end is in contact with the heart. A small fluid-inflatable balloon may be disposed at the distal end of the endoscope, outside of the transducer, so that the balloon is positioned between the transducer and the exterior surface of the heart, or the transducer may contact the heart directly. As in the previous embodiment, the saline or other fluid in the balloon couples the shock-waves generated by a shock-wave generator to the myocardium, providing more precise focusing of the energy. In an alternate embodiment, the transducer is located in the proximal end of the endoscope, with the shock-wave conducted to the distal tip using an appropriate transmission wire.

In yet another embodiment, a laser is coupled to an optical fiber which extends coaxially through a flexible catheter or flexible/rigid endoscope. A metal cap disposed at the tip of the catheter converts the optical energy into shock-wave energy, by inducing rapid tip motion to create highly localized cavitation effects. The distal end of the catheter (or endoscope) may include a fluid-filled balloon as in the previous embodiments to couple the shock-wave directly to the myocardium.

In still another embodiment, an extracorporeal lithotripsy device is used to direct focused shock-waves toward the myocardium. A fluid-filled balloon is inserted percutaneously into the space between the inner wall of the chest and the heart to conduct the shock-wave to the heart through a uniform medium.

The system and method of the present invention can also be utilized to augment conventional cardiac surgical procedures. For example, endoscopic cavitation system can be used to induce angiogenesis to initiate improved collateral circulation as an enhancement to, and/or backup for, bypass grafts. Alternatively, a miniaturized surgical ultrasonic cavitation system can be utilized to intra-operatively produce 1 mm channels in myocardium during a CABG procedure. Testing of such a system (Verdaasdonk, Cobelens—University Hospital Utrecht, The Netherlands) has demonstrated that the channels produced in this fashion are essentially identical (in terms of myocardial histology) to laser-produced TMR channels.

A shock-wave generator which has been used to induce cavitation effects for treatment of human disease is the extracorporeal shock wave lithotripsy ("ESWL") system commonly used for breaking up kidney or ureteral stones. These systems generally utilize a spark device and reflector to create a focused shock wave that penetrates tissue and impinges at great amplitude on the stone to be fractured by a combined shock-wave and cavitation effect. Smaller, and more focused systems are currently being developed in Europe for treatment of joints. The region of shock waves could be potentially controlled by the focusing reflector, leading to a larger area of myocardium receiving shockwaves/cavitation effects more uniformly than could be achieved via a laser TMR system.

An important aspect of the invention is that the shock waves are transmitted and focused only through tissue, water, or some other solid/liquid medium. Air spaces between the skin and the myocardium will preclude delivery of shock waves. In addition, shock waves travel differently in harder tissues, such as bone, and could be defocused by traveling through the ribs. Some implementations of the present invention utilize a fluid-filled balloon, inserted via needle, between the ribs, inflated, and utilized to transmit the shock waves to the myocardium. The shock-waves are applied to the balloon using minimally-invasive or entirely non-invasive methods, relying on the density uniformity provided by the fluid to conduct the shock wave energy to a localized region within the heart tissue.

As with laser TMR systems, it may be desirable to synchronize the shock wave with the heartbeat to occur at a specified phase (e.g., T-wave) of the beat. However, with sufficiently small amplitude shock waves, such synchronization may not be required. Various embodiments of the present invention may be utilized, incorporating synchronization or not. However, unlike the laser TMR systems, the amplitude of the shock wave delivered to the myocardium can be varied over a wide range with an extracorporeal shock wave system; this may allow cumulative doses of shock waves sufficient to induce angiogenesis, while further minimizing the myocardial tissue effects of the treatment.

As it has recently been found that certain proteins may modulate the effect of vascular growth factors, e.g., the angiopoetins, ANG-1 and ANG-2, another aspect of the present invention involves the combined use of these growth factor modulators and low-amplitude shock wave treatment using a system as previously described. While delivery of genes to upregulate expression of various growth factors could be performed simultaneously with the modulators, it may be desirable to first deliver the modulators, and then at a later time to stimulate growth factors. In this case, a non-invasive (or percutaneous—with shock wave transmitting balloon inserted via needle) approach would be preferable to catheter-based delivery of another agent into the myocardium.

BRIEF DESCRIPTION OF THE DRAWINGS

Understanding the present invention will be facilitated by consideration of the following detailed description of preferred embodiments of the present invention taken in conjunction with the accompanying drawings, in which like numerals refer to like parts and in which:

FIG. 1 is a diagrammatic view of a first embodiment of a system according to the present invention;

FIG. 2 is a diagrammatic view of a second embodiment of the present invention;

FIG. 3 is a diagrammatic view of a third embodiment of the present invention.

DESCRIPTION OF PREFERRED EMBODIMENTS

Figure 4:
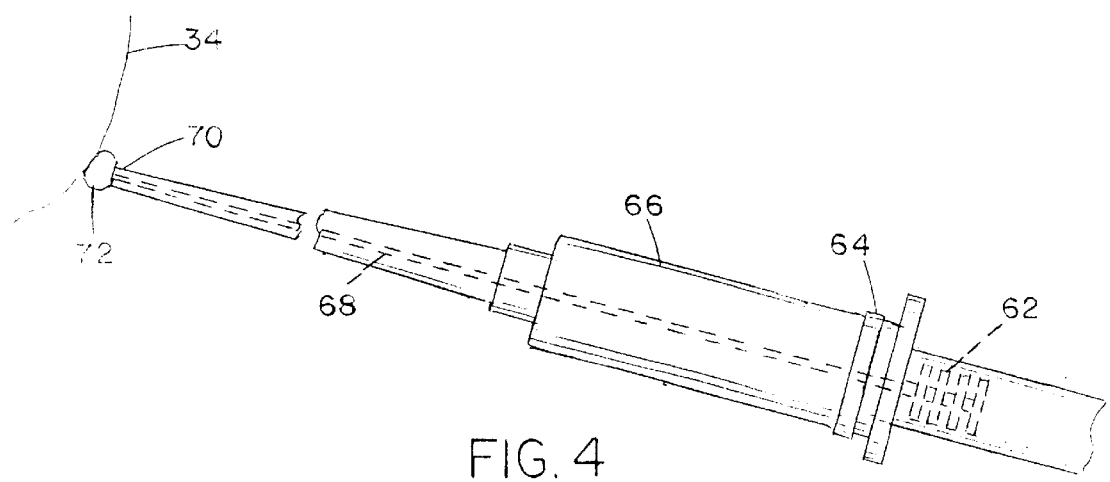
FIG. 4 is a diagrammatic view of a hand-held embodiment of the invention.

Each embodiment of the present invention utilizes a shock-wave generator of the type used for extracorporeal lithotripsy procedures, which generators are well known in the art. One such system is disclosed in U.S. Pat. No. 5,031,626 of Hassler, et al., where the shock wave generator has a planar circular membrane consisting of electrically conductive material. One side of the membrane is in contact with the propagation medium in the housing, and the opposite side of the membrane is covered by an insulating layer. A planar coil with spiral windings is disposed on the same side of the membrane, with the insulating 5a therebetween. The coil is connected via terminals to a high voltage pulse generator, by means of which the coil is charged with high voltage pulses. When the coil is charged with a high voltage pulse, the membrane abruptly moves away from the coil due to the effect of the magnetic field generated by the coil. As a result of this movement of the membrane, a pressure pulse is introduced into the propagation medium in the interior of the housing, and as it passes through the propagation medium, it is transformed into a shock wave. The shock wave propagates in the direction of a center axis of the shock wave generator.

An alternative source of the shock-wave can an opto-acoustic transducer such as that described in U.S. Pat. No. 5,944,687 of Benett, et al. The transducer is located at the end of an optical fiber which may be located within a catheter or other probe device. Energy for operating the transducer is provided optically by laser light transmitted through the optical fiber to the transducer. Pulsed laser light is absorbed in the working fluid of the transducer to generate a thermal pressure and consequent adiabatic expansion of the transducer head such that it does work against the ambient medium. The transducer returns to its original state by a process of thermal cooling. The motion of the transducer within the ambient medium couples acoustic energy into the medium. By pulsing the laser at a high repetition rate an ultrasonic radiation field can be established locally in the medium. The preceding descriptions are intended to be exemplary of the prior art as relates to shock-wave generating apparatus, and is not intended to limit the scope of the invention in any way.

As shown in FIG. 1, a first embodiment of the present invention illustrated a percutaneous implementation comprising a shock-wave generator 2 connected to a lithotripsy probe 4 adapted for insertion through a small incision in the chest wall 10, between ribs 12. Probe 4 is configured as a needle/cannular balloon system constructed in a manner similar to conventional balloon catheters and other devices used for angioplasty, hyperthermal treatment of tumors, and other medical procedures. The general construction for a balloon device is provided in U.S. Pat. No. 5,368,591 of Lennox, et al., which describes a heated balloon catheter. In the present invention, the heating wires are replaced with shock-wave transducers or transmission wires. A polyethylene teraphthalate (PET) balloon is mounted on nylon shaft. The balloon should be large enough to expand to fill the thickness of the space between the inner chest wall and the heart. The wall thickness of balloon is about 0.001 inch. For use in a catheter, a guidewire, which extends past the distal end of the catheter, may be used to guide the catheter through the vascular system or luminal structure.

In the present invention, the delivery device includes a cannula 5 containing a trocar 7 for making a puncture in the chest wall 10 and a balloon 6 at the distal tip of the cannula which can be inflated with fluid to fill the space between the inner chest wall and the myocardium 14. Fluid can be transferred into the balloon through a channel 9 in the cannula. Similarly, a channel may exist in the cannula for delivery of growth factors 11. Balloon 6 is fillable with a shock-wave transmissive fluid such as normal saline (0.9 percent NaCl in water). Syringe 8 provides means for controlling the inflation and deflation of balloon 6 via tubing connected to an inlet in balloon 6. The exterior of balloon 6 is preferably coated with a non-stick coating having a low coefficient of friction, such as silicon or polysiloxane.

Balloon 6 is inflated (e.g., with saline) to take up the space and contact the surface of the beating heart 14. Shock waves from the generator 2 and probe 4 are focused through the saline solution in balloon 6, as indicated by waves 16. Fluid-filled balloon 6 couples shock waves 16 to the myocardium, reducing hemolysis which could occur if the shock waves are transmitted through blood and potentially allowing more refined focusing than would be available, if the catheter contacted the myocardium directly.

As shown in FIG. 2, an endoscopic probe 24 could also be the shock wave coupler, where the shock waves are created by external (extracorporeal) generator 22. Probe 24 is inserted through an incision 28 in the chest wall 30 between ribs 32. The shock-waves can be communicated to the distal end of the probe by the transmission wire 25. Alternatively, electrical energy generated by generator 22 is transmitted through a wire 25 to the distal end of the endoscope to create a spark at a metallic cap 27. The response of the metal to the spark creates shock waves and/or cavitation effects. A flexible saline- or gel-filled sac or balloon 26 is located at the distal end of the probe 24 to contact the myocardium of the heart 34 and transmit the shock waves. Visualization of the target area can be achieved using known methods. A video-based viewing endoscope 36 is illustrated in the figure as a separate device, but may be incorporated into the endoscope using methods known in the art.

In an alternate embodiment, the cavitation effect is induced by ultrasonic vibration of a tip disposed at the distal end of the endoscope in an assembly similar to that disclosed in U.S. Pat. No. 4,223,676, of Wuchinich, et al., which is incorporated herein by reference. In that patent, an apparatus for the surgical removal of tissue is disclosed comprising a handpiece having a resonant vibrator with a magnetostrictive stack composed of a nickel alloy sandwich and a connecting body encompassing a hollow elongated tool which is ultrasonically vibrated at its tip longitudinally to a peak-to-peak stroke of at least 0.005 inches at about 25 KHz. A generator powers the vibrator and is automatically controlled at the frequency to maintain the resonant vibration. As applied to the present invention for treatment of cardiac disease, the tip, which is preferably titanium, has a distal diameter on the order of 1 mm, is solid, rather than hollow as disclosed in the '676 patent. The shape of the tip is selected to distribute its mass to maintain resonant vibration and will typically be tapered, having a larger diameter at its proximal end than at its distal end.

Such an ultrasonic needle device can be used in a manner similar to that disclosed relative to FIG. 2 except that it would be used to drill holes into the myocardium during open chest surgery or during minimal invasive CABG or thorascopic procedures. The cavitation effects at the needle tip provide a mechanism to dissolve muscular tissue and create channels in the myocardium similar to laser channels. The diameter of the channels would typically be up to 1 mm diameter.

FIG. 4 illustrates an exemplary structure for a hand-held probe 60 having a resonant stack 62, metal connector 64, which is formed from a material having a high characteristic acoustic impedance or an alloy such as monel. The connector is partially housed in housing 66. The resonant stack 62 is excited by electrical power provided by the generator, such as that generally referred to as the shock-wave generator in FIGS. 1 and 2. Connector 64 connects to tip 68 to transmit the resonant vibration to distal end 70 which can be placed in direct contact with the myocardium 34 or can have a fluid-filled balloon 72 interposed between the distal end 70 and the myocardium to conduct the vibration to the tissue. The frequency of the vibration is selected to induce cavitation in the tissue, and may be used to form channels through the myocardium that are normally associated with TMR. To avoid trauma, it may be preferable to avoid generation of the channels, and rely upon the cavitation effect to provide the therapeutic effect.

A device using the vibrating tip can be used transcutaneously as described relative to the embodiment of FIG. 2, or used as a hand-held tool in an open chest surgical procedure, where the surgeon has a clear view of the heart and can physically position the tip at desired locations on the myocardium. Viewing in either case may be enhanced by using an endoscopic viewing device incorporated in the probe. Such a hand-held system has the advantage of providing tactile feedback, so that the surgeon can feel how much pressure is being applied. This provides a significant advantage over laser TMR systems, which have no mechanism by which tacile feedback could be obtained.

The embodiment illustrated in FIG. 3, using the laser based method for inducing shock waves previously described, laser 42 is coupled to an optical fiber 43 which extends coaxially through a flexible catheter 44. The catheter is inserted using standard procedures through the femoral artery 48, up through the aorta across the aortic valve and into the left ventricle of heart 52, where it contacts the inner wall. A metal cap 46 disposed at the tip of the catheter converts the optical energy into shock-wave energy, by inducing rapid tip motion to create highly localized cavitation effects. The distal end of the catheter (or endoscope) may include a fluid filled balloon 47 as in the previous embodiments to couple the shock wave directly to the myocardium.

The laser approach could also be used with an endoscopic probe for use in minimally invasive CABG procedures. In this case, due to the wider available distal surface of the endoscopic probe, a phased array of shock wave generators could be placed to appropriately focus or direct the shock waves to the myocardium. Multiple shock-wave generators could be created using multiple fibers directed toward the same or different distal tip elements. Other means for generating shock-waves can be used, including electric spark methods, which are known in the art.

The system and method of the present invention can also be utilized to augment conventional cardiac surgical procedures. For example, endoscopic cavitation system can be used to induce angiogenesis to initiate improved collateral circulation as an enhancement to, and/or backup for, bypass grafts.

An important aspect of the invention is that the shock waves are transmitted and focused only through tissue, water, or some other solid/liquid medium. Air spaces between the skin and the myocardium will preclude delivery of shock waves. In addition, shock waves travel differently in harder tissues, such as bone, and could be defocused by traveling through the ribs the present invention makes use of a delivery system that conducts the shock-waves to the heart tissue to induce cavitation either by a mechanical device, i.e., endoscope, catheter, needle, or vibrating tip, or by ensuring a uniform transmission media between the point from which the shock wave emanates and the heart. Some implementations of the present invention utilize a fluid-filled balloon, inserted via needle, between the ribs, inflated, and utilized to transmit the shock waves to the myocardium. The shock-waves are applied to the balloon using minimally-invasive or entirely non-invasive methods, relying on the density uniformity provided by the fluid to conduct the shock wave energy to a localized region within the heart tissue.

It may be desirable to synchronize the shock wave with the heartbeat to occur at a specified phase (e.g., T-wave) of the beat, using techniques known to those of skill in the art. However, with sufficiently small amplitude shock waves, such synchronization may not be required. Various embodiments of the present invention may be utilized, incorporating synchronization or not. However, unlike the laser TMR systems, the amplitude of the shock wave delivered to the myocardium can be varied over a wide range with an extracorporeal shock wave system; this may allow cumulative doses of shock waves sufficient to induce angiogenesis, while further minimizing the myocardial tissue effects of the treatment.

It will be apparent to those skilled in the art that various modifications and variations can be made in the system and method of the present invention without departing from the spirit or scope of the invention. Thus, it is intended that the present invention cover the modification and variations of this invention provided they come within the scope of the appended claims and their equivalents.

What is claimed is:

1. A system for treatment of coronary disease comprising:
   a generator for producing a shock wave for inducing cavitation effect in myocardium functionally connected to
   a delivery system comprising an intracorporeal delivery portion for transmitting shockwaves directly to the myocardium;
   a fluid-inflatable balloon disposed at a distal end of the delivery portion; and
   a means for inflating and deflating the balloon wherein the system produces shockwaves in the myocardium.

2. The system of claim 1, wherein the generator comprises an extracorporeal shock wave lithotrypsy system.

3. The system of claim 1, wherein the generator comprises an electrical power source and a transducer, and the delivery system comprises a shock wave transmitting connector connected to the transducer and extending through to a distal end of an intracorporeal delivery portion wherein the intracoporeal delivery portion is selected from the group consisting of an endoscope, a lithotrispy probe, a hand-held surgical probe, and a catheter.

4. The system of claim 1, wherein the fluid-inflatable balloon is inflated using a saline solution.

5. The system of claim 1, wherein the generator comprises an electrical spark generator and a metal cap, and the delivery system comprises:
   a wire connected at a proximal end to the spark generator and at a distal end to the metal cap; and
   a delivery portion comprising a device for manipulating a position of the metal cap selected from the group consisting of an endoscope, a lithotripsy probe, a hand held surgical probe, and a catheter.

6. The system of claim 1, wherein the generator comprises an electrical power source and a transducer disposed between the generator and the intracorporeal delivery portion and the delivery system includes a connector for providing electrical power from the power source to the transducer.

7. The system of claim 6, wherein the delivery system further comprises a delivery device selected from the group consisting of an endoscope, an extracorporeal lithotripsy probe, a hand-held surgical probe, and a catheter.

8. The system of claim 1, wherein the generator comprises a laser and an electro-optical transducer for converting laser light into a shock-wave and the delivery system comprises:
   an optical fiber extending from an output of the laser to the electro-optical transducer; and
   a delivery portion comprising a manipulating device selected from the group consisting of an endoscope, a lithotripsy probe, a hand held surgical probe, and a catheter.

9. The system of claim 1, further comprising means for introducing one or more growth factor modulators either systemically or locally to the heart tissue.

10. A system for treating heart disease in a patient comprising:
    an extracorporeal shock-wave generator;
    a device for coupling shock waves from the generator to an outer chest wall of the patient; and
    a needle/cannula-balloon device for coupling shock waves from the coupling device to the myocardium comprising:
    a cannula;
    a shock-wave transmitting connector;
    a fluid inflatable balloon; and
    a channel within the cannula for transmitting fluid to the balloon.

11. The system of claim 10, further comprising a channel for introducing at least one growth factor modulator.

* * * * *